(12) United States Patent
Raup

(10) Patent No.: US 8,931,039 B2
(45) Date of Patent: Jan. 6, 2015

(54) METHOD AND SYSTEM FOR A DOCUMENT-BASED KNOWLEDGE SYSTEM

(75) Inventor: Gordon E. Raup, Roseville, MN (US)

(73) Assignee: Datuit, LLC, Roseville, MN (US)

( * ) Notice: Subject to any disclaimer, the term of this patent is extended or adjusted under 35 U.S.C. 154(b) by 830 days.

(21) Appl. No.: 13/113,831

(22) Filed: May 23, 2011

(65) Prior Publication Data

US 2011/0289549 A1 Nov. 24, 2011

Related U.S. Application Data

(60) Provisional application No. 61/347,711, filed on May 24, 2010.

(51) Int. Cl.
*G06F 21/00* (2013.01)
*G06F 19/00* (2011.01)
*G06F 21/62* (2013.01)

(52) U.S. Cl.
CPC .......... *G06F 19/322* (2013.01); *G06F 21/6218* (2013.01); *G06F 21/6245* (2013.01); *G06F 19/324* (2013.01); *G06F 2221/2141* (2013.01)
USPC .......................................................... 726/1

(58) Field of Classification Search
CPC ............ G06F 21/6218; G06F 21/6245; G06F 2221/2141
USPC .......................................................... 726/1
See application file for complete search history.

(56) References Cited

U.S. PATENT DOCUMENTS

| | | | | |
|---|---|---|---|---|
| 4,868,733 A | * | 9/1989 | Fujisawa et al. ...................... | 1/1 |
| 5,163,091 A | * | 11/1992 | Graziano et al. .............. | 713/176 |
| 5,191,613 A | * | 3/1993 | Graziano et al. .............. | 713/176 |
| 5,666,549 A | * | 9/1997 | Tsuchiya et al. .............. | 715/223 |
| 5,867,821 A | | 2/1999 | Ballantyne et al. | |
| 5,937,084 A | * | 8/1999 | Crabtree et al. .............. | 382/137 |
| 6,460,034 B1 | * | 10/2002 | Wical ..................................... | 1/1 |
| 6,574,742 B1 | | 6/2003 | Jamroga et al. | |
| 6,988,075 B1 | | 1/2006 | Hacker | |
| 7,260,584 B2 | * | 8/2007 | Hailey et al. .......................... | 1/1 |

(Continued)

OTHER PUBLICATIONS

Ginsburg et al.; Annotate: a Web-based knowledge management support system for document collections; Systems Sciences, 1999. HICSS-32. Proceedings of the 32nd Annual Hawaii International Conference on (vol. Track1 ); Date of Conference: Jan. 5-8, 1999; IEEE Xplore.*

(Continued)

*Primary Examiner* — Bradley Holder
(74) *Attorney, Agent, or Firm* — Winthrop & Weinstine, P.A.

(57) ABSTRACT

A document-based storage and knowledge production solution designed for use as a primary information system is disclosed. It uses Authentication, Privacy and Security Standards to ensure the source and reliability of the information in the stored documents. It uses Information and Document Standards to explicitly define the information content held in each document. Electronic documents from separate authors, from the same or separate legal entities, are stored together in the same system and can be used in aggregate for the generation of new knowledge. Variations are used to accelerate response times. Other variations describe the method's use as a Variable Electronic Health Record System in which different parts of the system can be produced by separate manufacturers. This is possible because the underlying document-based knowledge system stores the separate documents from each manufacturer's system in such a manner that they can be understood by systems from other manufacturers.

29 Claims, 4 Drawing Sheets

(56) References Cited

U.S. PATENT DOCUMENTS

| | | | |
|---|---|---|---|
| 7,472,345 B2 * | 12/2008 | Hailey et al. | 715/234 |
| 7,613,620 B2 | 11/2009 | Salwan | |
| 7,885,822 B2 | 2/2011 | Akers et al. | |
| 7,925,610 B2 * | 4/2011 | Elbaz et al. | 706/55 |
| 7,945,567 B2 * | 5/2011 | Delic et al. | 707/728 |
| 8,155,951 B2 * | 4/2012 | Jamieson | 704/10 |
| 2004/0172307 A1 | 9/2004 | Gruber | |
| 2004/0186824 A1 * | 9/2004 | Delic et al. | 707/3 |
| 2005/0038670 A1 | 2/2005 | Takkar et al. | |
| 2005/0080808 A1 * | 4/2005 | Hailey et al. | 707/102 |
| 2005/0080814 A1 * | 4/2005 | Hailey et al. | 707/103 R |
| 2005/0081144 A1 * | 4/2005 | Hailey et al. | 715/513 |
| 2005/0154614 A1 | 7/2005 | Swanson et al. | |
| 2005/0154983 A1 * | 7/2005 | Hailey et al. | 715/530 |
| 2007/0016450 A1 | 1/2007 | Bhora et al. | |
| 2008/0183691 A1 * | 7/2008 | Kwok et al. | 707/5 |
| 2008/0228040 A1 | 9/2008 | Thompson | |
| 2009/0187425 A1 | 7/2009 | Thompson | |
| 2010/0063799 A1 * | 3/2010 | Jamieson | 704/9 |
| 2010/0179852 A1 | 7/2010 | Tomizuka et al. | |
| 2010/0299155 A1 | 11/2010 | Findlay et al. | |

OTHER PUBLICATIONS

Eirund et al.; Knowledge based document classification supporting integrated document handling; Proceeding COCS '88 Proceedings of the ACM SIGOIS and IEEECS TC-OA 1988 conference on Office information systems; 1988; pp. 189-196; ACM Digital Library.*

Jiye An, Xudong Lu, Huilong Duan, "Integrated Visualization of Multi-modal Electronic Health Record Data," The 2nd International Conference on Bioinformatics and Biomedical Engineering (iCBBE 2008), May 16-18, 2008, pp. 640-643, IEEE, Shanghai, China.

Charalampos Doukas, Thomas Pliakas, Ilias Maglogiannis, "Mobile Healthcare Information Management utilizing Cloud Computing and Android OS," Engineering in Medicine and Biology Society (EMBC), 2010 Annual International Conference of the IEEE, Aug. 31-Sep. 4, 2010, pp. 1037-1040, IEEE, Buenos Aires, Argentina.

Kenneth D. Mandl, Isaac S. Kohane, "No Small Change for the Health Information Economy," The New England Journal of Medicine, Mar. 26, 2009, pp. 1278-128, Boston, Massachusetts, USA.

Integrating the Healthcare Enterprise International, Inc., "Cross-Enterprise Document Sharing," http://wiki.ihe.net/index.php?title=Cross_Enterprise_Document_Sharing, Mar. 2, 2011.

Nathan Hulse, Roberto Rocha, Richard Bradshow, Guilherme Del Fiol, Lorrie Roemer, "Application of an XML-based Document Framework to Knowledge Content Authoring and Clinical Information System Development," Proceedings of the American Medical Informatics Association Annual Symposium 2003, AMIA Annu Symp Proc. 2003, p. 870.

Hsinchun Chen, Vasant Dhar, "A Knowledge-Based Approach to the Design of Document-Based Retrieval Systems," COCS '90 Proceedings of the ACM SIGOIS and IEEE CS TC-OA Conference on Office Information Systems, Apr. 1990, pp. 281-290, Association for Computing Machinery, New York, New York, USA.

Mark Ginsburg, "Annotate a Web-based Knowledge Management Support System for Document Collections," Doctoral Thesis, New York University, Sep. 1998, available at http://citeseerx.ist.psu.edu/viewdoc/summary? doi=10.1.1.39.6336.

* cited by examiner

Fig. 3

METHOD AND SYSTEM FOR A DOCUMENT-BASED KNOWLEDGE SYSTEM

BACKGROUND

Almost all Electronic Health Record Systems ("EHR-S"), store information in Relational Database Management Systems ("RDBMS"). RDBMS are an improvement over the previously used flat file database technology which, based on a relatively rigid table-like structure of columns and rows, was inflexible, did not lend itself to ongoing maintenance modifications, such as adding or removing columns, and which became dramatically slower as the volume of data stored in those databases grew.

RDBMSs, although unquestionably an improvement over flat file technology, also suffer from various drawbacks. RDBMSs are based on storing data in numerous separate tables, which are linked together via mechanisms such as Primary Keys and Foreign Keys into what are collectively called databases. A single patient's EHR data may be spread over hundreds of different tables, and can only be presented to the user, after significant computer processing to follow the links from one table to the next and to then combine the collected data into either human- or machine-intelligible information. This limitation effectively means that the end user is dependent on the software manufacturer that designed the database. For all practical purposes, the end user is not able to view or use the data in the EHR-S database—even though that data belongs to the end user—without doing so in a manner approved by the software manufacturer. Moreover, the end user is not able to modify the structure and operation of the EHR-S without the permission and support of the software manufacturer. This situation puts significant control in the hands of the software manufacturer, resulting in substantially higher costs to the end user and a substantial brake on innovation.

Another problem in the related art is the difficulty the Health Information Technology ("HIT") industry is having in developing effective ways of sharing health data. It is widely recognized that the power of electronic health records cannot be fully utilized until these records may be easily and quickly shared as the need arises, and yet do so in a manner that preserves the confidentiality of patient health information. There is little disagreement that solving this problem will lead to major benefits including the following:

The close collaboration of multiple providers in determining and delivering care to the individual patient, in contrast to the prior art, in which each provider has substantially difficulty obtaining, in a timely manner, detailed and accurate information about the care being provided by other healthcare providers;

The resilience of the health care system to natural and human disasters that destroy all health data within a geographic area, by having duplicates of the data ready to replace the destroyed data at a moment's notice; and The development and improvement of healthcare procedures and regimen, by allowing sustained research on substantially larger and richer aggregations of health data than are now practical.

These benefits, though powerful, have proved elusive because of the architecture of currently available EHR-S. Presently, health data in the United States is stored in hundreds of thousands of separate databases in tens of thousands of different locations. Creating a National Health Information Network ("NHIN") to seamlessly and effectively share data across all of those potential points of failure has proved to be a daunting task.

There have been two major approaches in the related art to solving this problem: the Federated Model and the Centralized Model. In the centralized model, a copy of the health data is stored centrally in community or regional databases. In the federated model, the healthcare providers in a given area register with the regional Health Information Exchange ("HIE") but don't actually share data until that data is requested by a specific user.

Both methods have exhibited substantial problems in meeting the objectives of the NHIN. The centralized model is clearly better suited towards meeting those objectives. Indeed, the federated model does not adequately meet any of the above objectives. The objectives of resiliency and large volume research are not really possible as long as the data is locked in thousands of different databases controlled by thousands of separate governance authorities. The objective of enabling care collaboration is partially met, in that the provider can, usually, request and receive information on the patient's care from other providers. However, due to the federated nature of this approach, this information is not available in a timely manner, nor is the information flow reliable, due to the many points of potential failure.

Despite those difficulties with the federated model, the centralized model has an even more serious problem: few stakeholders have been willing to absorb the expense of maintaining the considerable amount of patient data at centralized locations. Those places where the centralized model has been attempted have not been successful, except to the extent that government and philanthropic bodies have agreed to fund the effort.

As a result, most viable efforts at establishing HIEs are using the federated model. The federated model is cheaper, but there have still been problems building a business case among the stakeholders for supporting the ongoing expense of the HIE. Nevertheless, federated HIEs are being successfully deployed. The usefulness of these federated HIEs, however, remains to be proven.

As mentioned above, federated HIEs have issues with data availability. Since the data is stored at numerous sites not controlled by the HIE, the requesting organization doesn't really know what health data for the patient is available until it is requested. Moreover, the particular information may be stored at a facility that is currently offline. As a result of these difficulties, the federated model of HIE is not very reliable for the task of care coordination unless the parties to the exchange have an ongoing business relationship before the exchange or the originator of the data exchange is the sender and not the receiver. In other words, federated HIEs are successful at sharing data between business partners and at sending data from one provider to another. They have not, however, been very successful at informing care providers about the activities of non-business partners. Thus, federated HIEs, while a viable enhancement of previously existing interface technology, have had limited success at improving care collaboration.

Federated HIEs have been shown to be successful at providing a mechanism for providers to submit required data to regulatory authorities and voluntary quality improvement organizations. However, while this ability is clearly beneficial, it is not really an enhancement over what is available with point to point transmission between business partners, such as with web service exchanges. It simply provides a more expensive way of achieving the same result (because the HIE in the middle must be paid for).

Beyond these multiple problems with federated HIEs there is a significant data validity risk with all current Health Information Exchanges, whether they use the federated model or the centralized model. Currently health information is stored in hundreds of thousands of proprietary databases designed and maintained by one of the hundreds of vendors offering EHR-S system. Before information can be exchanged, it must be extracted from these systems and translated to a common format understood by both the sending and receiving systems. At the receiving end, the information must be translated again into a format compatible with the receiving system's design. As a result, the data is displayed and used at the receiving end in a different format and context than it was originally created in. This runs the risk of potentially serious translation errors.

Due to all of the various issues listed above, and other unlisted issues, the goal of large-scale data sharing for care collaboration, health data resiliency and large-scale research has so far been unmet.

We have discussed several major problems with the prior art currently used in health information technology. The two most problematic of these issues has been the high cost and inflexibility of EHR-S and other HIT systems, and the inability to achieve an effective health information network despite many efforts and high costs. Both of these problems are consequences of the legacy architecture of storing health data in many separate databases created by hundreds of vendors with widely different design objectives.

SUMMARY

To solve these problems, as well as others, aspects of the present invention provide a system in which data is stored in separate discrete units (collectively, though not limiting, "documents") instead of databases. Effective control of the documents is managed by the owner or license-holder of the system in order to ensure the integrity and validity of the data in each document and to ensure the consistency and the compatibility of the data in one document to data in other documents controlled by the system. As a part of this effort, the owner of such a system may establish rules to control the syntax or semantics of the data allowed into the documents so that data from one document can be reliably combined with data from other documents. This system is termed a Document-Based Knowledge System ("DBKS").

Some implementations of a DBKS may specify that the documents controlled by the system be stored remotely in internet-connected data centers. Some such DBKS may automatically backup each document in two separate remote datacenters in order to ensure recovery from natural and man-made disasters. For a healthcare focused DBKS, such an implementation may allow all of the documents about a specific patient to be stored in one common datacenter, regardless of how many different provider organizations create documents controlled by the DBKS. Such a DBKS may also require documents to be formatted in accordance with standards specified by recognized national and international Standards Development Organizations.

Some implementations of such a DBKS may also establish rules for how the data stored in such documents may be collected from end-users so that software programs from multiple different software manufacturers can be used interchangeably at the discretion of the persons or other entities creating the documents. One such exemplary implementation of a DBKS is termed a Variable Electronic Health Record System, or VEHRS. In a VEHRS, healthcare providers can modify small parts or large parts of the VEHRS without the permission of the manufacturer of those sections, by simply replacing those sections with components from another manufacturer. This allows the healthcare provider substantially greater control over its EHR-S than is available with the prior art currently available in the marketplace.

Such a VEHRS (and its underlying DBKS) substantially eliminates the problems discussed in the previous section, as follows:

There is no need for Health Information Exchanges, using either the federated or centralized model, because the data for each patient is automatically stored in the same location and available to all healthcare providers caring for the patient without such time consuming and expensive exchanges, provided that the patient give permission for each provider to access documents created by the other providers. Care coordination is easier with all data for the patient available to all of the patient's providers without meaningful time delay.

No translation of the information is needed from one vendor's system to another's because the DBKS enforces such rules as are needed to ensure that both vendors' systems always understand documents created by any vendor's system that conforms to the rules of the DBKS.

The costs that are now being borne to support HIEs will shrink dramatically because the basic cost of storing data in a DBKS is borne by each healthcare provider using the system. Moreover, the cost to that provider, both to store their data in the DBKS and to use VEHRS complaint software to create, view, use and distribute that data, will be substantially less than they pay now for storing the data on local servers using single-manufacturer software. These benefits are due to both the efficiency of large scale datacenters and the change in power relationships relative to control of the data. Note for example, that such a VEHRS might allow open-source developers, including healthcare provider organizations themselves, to develop components of the VEHRS, thus putting substantial downward pressure on costs of the EHR-S implemented within the VEHRS.

Data resiliency is automatically maintained since each electronic document is stored in multiple locations by design. Note also that the likelihood of restoring the damaged data is enhanced by the fact that data is stored in documents instead of databases. Every recovered document stands by itself without need for any other documents to be recovered. This approach contrasts to the situation when the health data is stored in isolated databases. Generally speaking, unless a large fraction, if not all, of the database is recovered, none of it will be usable.

Finally, the massively large DBKS document collection in an exemplary implementation will be available for research at a fraction of the current cost for research. This is because the data is already available in the cloud and is already formatted properly is accordance with national and international standards. The issues of gaining informed consent from the patient, then getting the labor time of the provider organization to extract and send the data, and then translating and scrubbing the data so that it can be combined with data from other sources, all but disappear.

Additional advantages and novel features in accordance with aspects of the present invention are set forth in the description that follows, and will become apparent to those skilled in the art upon examination of the following.

DESCRIPTION OF THE DRAWINGS

FIG. 3 is a view of a display screen for an exemplary embodiment of the end user software of a Variable Electronic Health Record System.

DETAILED DESCRIPTION

Figure 1:
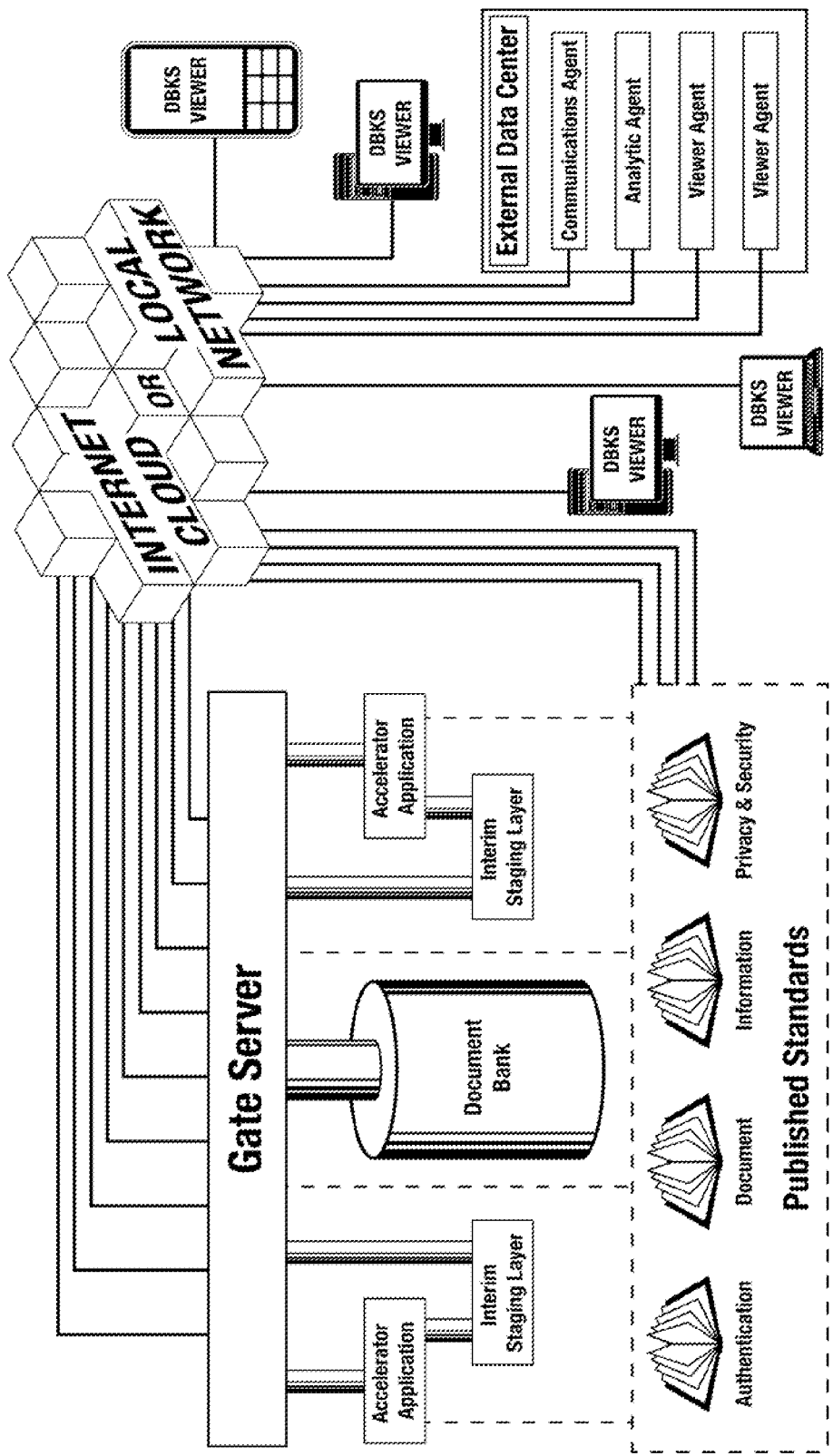
FIG. 1 is a schematic view of one embodiment of a Document-Based Knowledge System.

We have introduced two names to describe aspects of the present invention, the Document-Based Knowledge System (DBKS) and the Variable Electronic Health Record System (VEHRS). We will now discuss the characteristics of each of these concepts and describe the details of several implementations of each one, along with showing how the VEHRS uses a DBKS foundation in order to meet its design goals.

Characteristics of a Document-Based Knowledge System

The DBKS is a method of storing and retrieving data from electronic data storage devices and creating new information therefrom that is distinctly different from the prior RDBMS art currently in use. The characteristics for a DBKS are:

1. Permanent storage of the information protected by the DBKS ("Protected Information") is in discrete electronic documents.
2. No Protected Information is accepted by the DBKS for permanent storage until the provider of that information has been authenticated ("Authenticated User") in compliance with published standards for who is allowed to contribute information to the DBKS ("Authentication Standards").
3. Each document accepted into the DBKS is strongly protected to prevent any alteration of the document by processes not under the control of the DBKS ("Protected Documents").
4. Each Protected Document and other information accepted into the DBKS is strongly protected against access by unauthorized entities by the enforcement of strong privacy and security standards for who is allowed to access what information in what circumstances ("Privacy and Security Standards").
5. Once a Protected Document is accepted into the DBKS, it is should not be modified by the DBKS to change its semantic or syntactical meaning.
6. The Protected Information in each Protected Document is structured in compliance with published standards for that information ("Information Standards") and the standard(s) to which each unit of information asserts compliance are unambiguously referenced in the document.
7. Each Protected Document is structured according to published standards for the type of document it asserts to be ("Document Standards") and the standard(s) to which it asserts compliance are unambiguously referenced in the document.
8. New information is created by the DBKS by combining, synthesizing, calculating, or otherwise deriving the new information from the units of information in the existing Protected Documents.
9. The DBKS is the primary mechanism used by Authenticated Users for the storage of the Protected Information submitted to the method.

These characteristics of a DBKS are an expression of the long-standing design principle generally known as "garbage in, garbage out." Unless you ensure that the information going into the system is accurate and reliable, you will not be able to rely on the information created by combining that information in different ways. The first seven characteristics for a DBKS listed above ensure that the information is from reliable sources, that it is protected against exposure or tampering, that it is structured in such a way that the individual units of information are unambiguously defined, and that the units of information haven't be altered since they were accepted into the DBKS. In other words, there is no "garbage in." The eighth characteristic is that the DBKS is thus able to create new information that is itself accurate and reliable. Since there is no "garbage in," we can be confident that there will be no "garbage out." The ninth characteristic, that the system be the primary method for storing the protected information, ensures that the first eight characteristics are implemented with the rigor required for a DBKS. If the system is simply used for secondary purposes such as data mining or communicating with third parties, but not used for the primary mission of its users, it will not be held to the same standards to which a primary system is held and thus will not implemented with the rigor sufficient to be a knowledge system.

A key feature of a document-based knowledge system described herein is that each document in the system is understandable on its own, without reference to the other documents in the system, and with minimal machine processing. Moreover, what processing is required to render the document intelligible to humans is itself specified within the document by referencing the various information and document standards to which the document asserts compliance. Thus, the information within each document is human-readable without an intimate knowledge of the inner workings of the DBKS.

For example, a Continuity of Care Document ("CCD"), which is specified at the time of this writing in several regulations of the United States Department of Health and Human Services, based on a specification developed by Health Leven Seven ("HL7"), an accredited Standards Development Organization ("SDO"), requires the document to be displayed using the eXtensible Markup Language ("XML"), a document standard widely supported by most internet browsers. Thus, an individual CCD can be removed from storage and displayed in human-readable form without knowledge of the underlying system from which is was removed. By specification, a CCD contains all the information needed to meaningfully act on its contents, including the patient's name, identifying numbers, the name and contact information of the healthcare provider organization that created the CCD, and if appropriate to the purpose of the CCD, the patient's primary physician, principal diagnoses, current medications, and known allergies.

In sum, the information in and knowledge derived from a DBKS is highly reliable and fault tolerant because the information is stored in separate small documents. Each document is accepted into and maintained by the system as a semantic and syntactical whole, thus drastically reducing the number of points of potential human and machine failure. This also meets our design goal of reducing the dependence of the end user on the assistance of the vendor that created their information system, because the documents can be read and understood outside of the DBKS without the assistance of the vendor since all of the information to do so is either in or referenced by the document.

Further, regarding our design goal of enabling tight real-time collaboration between all of the healthcare providers caring for a patient, a document-based knowledge system allows End User Software solutions from different vendors to each store their information in the form of Protected Documents in the DBKS and read the Protected Documents stored by other vendors' systems without having detailed knowledge of the internal workings of the system. They simply need to know how to form and interpret documents compliant with the published Documents Standards containing information compliant with the published Information Standards (and abide by the published Authentication Standards). Thus, with a DBKS, all of the information from all providers caring for a patient can kept in the same location and new knowledge generated using all of the information about the patient, not just the information created by one provider. This is not possible with database management systems, which require a detailed knowledge of the underlying database in order to store information into it, unless all of the providers caring for the patient use systems from the same vendor. We will discuss this further when describing the VEHRS below.

Issues with System Response Times

A DBKS is significantly more storage intensive and processing intensive than a DBMS. For example, modifying a document requires duplicating the document, making the necessary modifications, including information about what was changed, why, and by whom and adding a linkage back to the previous version of the document. This is much more storage and processing intensive than simply changing some columns in a database row. Even more restrictive is the issue of response time. Users of modern information systems need to receive the information they request in near-instantaneous time-frames from the user's point of view. For example, Google has reported that the rate of follow-on clicks begins dropping when their response time goes over 600 ms. Similarly, some EHR-S manufacturers report design goals of a 1-3 second response time, though routinely fail that goal. If a DBKS waited until the user requested information to begin searching for that information in a large document bank holding hundreds of thousands of Protected Documents, it would never be able to respond in a timely enough manner to meet users needs, even with its inherent advantages. To be able to match or exceed the response times of the prior art, a DBKS needs to employ substantial pre-processing and interim storage mechanisms so that the requested information has in most cases already been prepared for delivery before the request is received. Thus, while a DBKS can be built without technology to accelerate system response time and be novel in relation to the prior art, it is not likely to be commercially viable without acceleration technology. In recognition of this fact, we provide, in several exemplary variations of the DBKS, support for four technologies to accelerate system response time: document metadata, of which we describe three types, Entity Summary Documents, Document Maps and Entity Maps, whose purpose is to permanently store key units of information from the Protected Documents to speed searching; temporary high-scalability storage, which we call Interim Staging Layers, whose purpose is to temporarily store information likely to be requested by end users or used in searches; Accelerator Applications which run under the control of the network server, whose purpose is to predict user requests and prepare the response before receiving the request; and Data Agents, which can be used for multiple purposes, including the preparation of display pages for the end user software in order to speed response time.

Main Components of a Document-Based Knowledge System

There are seven main components to any DBKS: four types of standards that all users of the DBKS should comply with (Document, Information, Privacy and Security, and Authentication standards), a storage facility to store the Protected Documents, server software to control access to the documents and create new knowledge from the existing documents, and end user software to present information from the system to the user and receive input from the user. For the purposes of this document, we are calling the later three components the Document Bank, the Gate Server, and the Viewer, respectively. In other exemplary implementations of a DBKS, as previously mentioned, we also describe the use of Entity Summary Documents, Document Maps, Entity Maps, Interim Staging Layers, Accelerator Applications, and Data Agents to speed system response time. All of these components and documents can be built with existing technology. The novelty of this invention is the method in which these components are used in conjunction with each other to create a commercially viable knowledge system in which permanent storage is performed in small self-explanatory chunks (i.e. electronic documents) instead of large databases that tie the end user to a single vendor.

Defined Standards for Use in a DBKS

There are four types of standards any implementation of the DBKS should specify and that all users of the DBKS should comply with: Authentication Standards, Document Standards, Information Standards, and Privacy and Security Standards. The presence, maintenance, and enforcement of these standards is one of the aspects that sets a DBKS apart from a generic document-oriented database solution available in the prior art. These published standards are visually depicted in FIG. 1.

Authentication Standards determine who is allowed to have access to the system and ensures that each time the user logs into the system that they are in fact who they say they are. There are many authentication standards currently available that may be used in implementations of the DBKS. The available standards range from low end solutions that are easy to implement and use and available at minimal cost such as the OpenID standard available from the OpenID Foundation, to high end solutions that are difficult and expensive to implement and not nearly as easy to use, but which provide the highest level of assurance that users accessing the system are who they say they are. An example of the later is the SAFE-BioPharma standard from the SAFE-BioPharma Association. The choice of which Authentication Standard to use is based on the specific needs of individual DBKS implementations.

Document Standards specify the structure and content of a specific type of document. Again, there are a range of document standards currently available. One exemplary implementation for the healthcare industry may use the various document standards published by HL7 and built on its Clinical Document Architecture ("CDA"), including the CCD described earlier, the CDA Consultation Note, the CDA History & Physical Note, the CDA Unstructured Document specification, and other document standards built on this architecture in addition to the Digital Imaging and Communications in Medicine ("DICOM") set of document standards for storing and exchanging images. Different implementations of the DBKS may employ or support different document standards.

Information Standards specify the structure and content of individual units of information contained within the documents or other information accepted by the method. For example, to specify the route by which a medication is administered to a patient, HL7 Version 2.5.1 has a defined standard for how such information should be coded, and the United States Food and Drug Administration ("FDA") has a different standard for the same unit of information. DBKS implementations may specify which units of information require conformance to one or more information standards and what the acceptable information standards are for those units of information.

Privacy & Security Standards specify who can have access to what information, about whom, and in what circumstances. In this area, implementers of a DBKS do not have a set of clear choices as they usually do with Authentication, Document, and Information standards. Here there are overlapping and sometimes conflicting standards to combine and resolve. In the healthcare field, regulations issued by the US Department of Health and Human Services pursuant to the Health Insurance Portability and Accountability Act of 1996 as amended are augmented in some states by state laws. The US Federal Trade Commission has additional regulations to limit identity theft. Other industries, such as financial services, have additional regulatory requirements. Such differing regulatory requirements may apply differently to different implementations of the DBKS. In addition, requirements of the end users need to be considered. A DBKS can store, retrieve and mix documents and other information from multiple separate legal entities. Users of such a method will undoubtedly want to have restrictions in place regarding who can access their information. Each implementer of a DBKS will need to take all of these factors into consideration in developing the Privacy and Security Standards that they will enforce in their implementation of a DBKS.

Gate Servers and Document Banks

Document Banks and Gate Servers are closely connected and may be implemented in pairs, with one Document Bank controlled by one Gate Server at the same physical location. FIG. 1 depicts a Gate Server and a Document Bank and the way in which they work together to implement the DBKS in coordination with the other elements of the method. Also see item D of FIG. 2 for a visual description of several Gate Server Document Bank combinations embedded into a Variable Electronic Health Record System as described further below. A Gate Server and Document Bank may be located in a state of the art datacenter with the following characteristics: robust physical security controls, including multiple layers of physical and electronic locks that can only be opened by a limited and known set of vetted personnel; strict environmental controls to ensure 100% compliance with established temperature, humidity, and air circulation standards, and redundant power sources including electrical generation capacity sufficient to fully power the datacenter for 72 hours or more, which are both tested and used frequently. Most implementations use datacenters with support for geographically remote backup.

Some implementations of the Document Bank use industry standard Storage Area Networks using hot-swappable hard disk drives in various Redundant Arrays of Inexpensive Disks ("RAID") configurations. Some implementations of the Document Bank may use other forms of accessible storage to optimize the Document Bank for its specialized task of storing and retrieving documents.

Management of the method is performed by the Gate Server. The Gate Server, as referred to herein, is a set of software components that performs multiple functions, including those listed below. Among those functions of the Gate Server is the storage and retrieval of documents into and out of the Document Bank. Some implementations achieve this function using existing industry standard network server hardware and commercially available document database software. Some implementations of the Gate Server use other specialized hardware and software methodologies for storing and retrieving documents.

Functions of the Gate Server Software Components

As part of a complete server software solution, the Gate Server software components should perform the following functions:
1. Authenticate the identity, rights, and privileges of any entity attempting to communicate with the Gate Server before establishing a communications session with that entity and terminating the communications channel with any entity that fails authentication before any information, except information needed for communications and authentication, is sent to the entity;
2. Validate that the transmission of each document and other information to a specific authenticated entity is in compliance with all applicable privacy and security standards and all applicable authentication standards before that document or other information is sent to that authenticated entity;
3. Validate that each unit of information received from an authenticated entity or created by processes controlled by the Gate Server is in compliance with all applicable information standards before accepting the information for storage, control, and use by the method;
4. Validate that each electronic document received from an authenticated entity or created by the method is in compliance with all applicable document standards before accepting the document for storage, control, and use by the method;
5. Create new documents and other information for storage, control, and use by the method by combining and synthesizing information from electronic documents or other information controlled by the Gate Server and by calculating or otherwise deriving new information from the existing information and documents controlled by the Gate Server;
6. Receive and fulfill, partially fulfill, or reject requests from authenticated entities for documents and other information in accordance with all applicable privacy and security standards and all applicable authentication standards;

Internally, the Gate Server software components may fulfill these functions in a variety of ways using industry-standard programming techniques and structures that are up to each implementer of a DBKS to determine. Externally, the Gate Server receives requests for Protected Documents and other information from running instances of the end user Viewer and from any Data Agents that may be active in some implementations, which collectively we will call External Requestors. Each implementer of a DBKS specifies the methods for External Requestors to request and receive information from the Gate Server. Most commonly, this is accomplished by defining a set of web services that the Gate Server fulfills, typically using Web Services Description Language ("WSDL"). These services can be requested and fulfilled using several common methodologies, including Simple Object Access Protocol ("SOAP") and Representational State Transfer ("REST").

Exemplary Web Services

In one exemplary implementation of a DBKS, the following set of Web Services may be fulfilled in addition to other services not described here:

1. Register User. This function is used to register a new External Requestor instance. This is performed by an existing Registered User that has the right to register new External Requestors. Once the External Requestor has been registered with the system, it receives a User ID and becomes a Registered User. Only Registered Users are allowed to submit or receive Protected Documents and other information to or from the Gate Server.
2. Open Work Session. This function is used to initiate a new work session for a Registered User. The function checks to make sure that the Registered User is in good standing and authorized to receive documents or otherwise interact with the system. The function may set up an internal work session for the Registered User and return a Work Session ID. The work session may contain information on the rights and privileges of the Registered User and set a length to the work session based on current policies. It may also start a fresh audit trail to record what Protected Documents and other information are requested by or delivered to the Registered User.
3. Submit Documents. The Registered User may use this function to submit one or more new documents to the Gate Server for storage in the Document Bank. The request may be sent with the User ID and the Work Session ID, which may be validated by the Gate Server before proceeding further. A separate Gate Server thread may then be launched to validate each of the submitted documents using the current Information and Document Standards and reject any that fail validation. In some implementations, additional execution threads may be launched to create a Document Map for each new document. If the submission fails for any reason, an appropriate error message may be returned to the Registered User and logged in the Gate Server Error Log. If the submission is successful, this service may send a response to the Registered User that the submitted document(s) have been accepted and stored and can now be considered Protected Document(s).
4. Retrieve Documents. This request may be sent with the User ID, Work Session ID and the Document IDs of the various requested documents. The rights of the user are checked against the current Privacy and Security Standards and the Authentication Standards. If all checks are successful, the requested Protected Documents and other information are returned to the External Requestor.
5. Find Documents. This request may include the User ID, Work Session ID and a query properly formatted according to the rules of the implementation. The Gate Server may first validate the User ID and Work Session ID and then perform a cursory high level inspection of the query to make sure it appears to be asking for information that is appropriate for this User. If this cursory high-level inspection fails, an error message may be returned and logged and the Work Session terminated. If it passes, the Gate Server may spawn a new thread to execute and validate the query. Depending on the nature of the query and the execution time to parse and run the query, some results may be returned before the query has completed to minimize total response time. Each Document returned may be compared specifically with the rights of the User to receive it. If any are found to exceed those rights, the response may be terminated with an error message and the Work Session may be terminated. Every document delivered to the External Requestor may be logged in the audit trail for the work session.
6. Create Document. This function may be similar to the Find Document function in that it may include a query to locate a set of documents. This portion of both functions may be handled similarly. Beyond that, however, the Create Document function may include instructions to extract data from the located documents and use it to create a new document. For example, a Find Document call may request all documents recording visits Mary Jones made to her pediatrician in the last 90 days. If there were seven visits, then most likely seven documents would be returned detailing what occurred in those visits. A Create Document request might instead request to extract all vitals and lab results from those found visit documents and create a new trend report document with that information. In the later case, the Query thread may parse and extract the requested data, create a new document according to published standards and stored the extracted data into the new document. This new document then becomes a new Protected Document with its own Document ID and Document Map. It contains sufficient information to be interpretable on its own (such as the names and IDs of Mary Jones, her doctor, and possibly her clinic, as well as the visit dates of each of the seven visits) just like any other document controlled by the method. In this implementation, the new document is returned to the External Requestor along with the Document Map for that new document.
7. Close Work Session. This function completes a work session and packages up and stores the audit trail for that session. If a Close Work Session call is never received, the Gate Server may automatically close the work session after a predetermined time period, which may be set up during processing of the Open Work Session call.
8. Specify Entity. This function may be used to either create a new entity in the method or modify an existing entity. After checking user rights as previously described, the Gate Server searches to see if the entity already exists in the system. If an exact match is found, the existing Entity Summary Document and Entity Map would be modified as requested and the new documents returned to the External Requestor. If a partial match (above a specified matching threshold) was found, the Gate Server would return a conflict error with the Entity Map for each of the conflicting entities in order for the user to resolve the conflict. If a match was not found, a new Entity Summary Document and Entity Map would be created and returned. The Specify Entity request may also include information about relationships of the entity to other entities in the system.
9. Specify Relationship. This function may be used to create or modify relationships between entities already existing in the system.
10. Find Entity. This function may be used to find unknown entities that have a specified relationship with specified entity. The External Requestor may submit an Entity ID with a Relationship Type or a Relationship Class, if such are enabled in the implementation, and the Gate Server would return a list either a list of Entity IDs or a set of Entity Maps that fulfill the request.
11. Combine Entities. This function may be used when it is discovered that two Entity Summary Documents, each with their own Entity Maps, exist for the same person or entity. In the healthcare industry this request may require a higher level of user rights and may require confirmation before it is performed, as it could have the effect of, for example, combining two patient charts.

The above are some of the main functions that may be implemented in an exemplary Gate Server implementation. Other functions may also be implemented.

Viewer Software

End users interact with the method with a variety of end user software solutions generically termed Viewers. FIG. 1 visually depicts a DBKS Viewer and how it interacts with other parts of the DBKS. Also see item C of FIG. 2 for an example of several Viewers implemented as a part of a wider VEHRS. Different implementers may offer widely different implementations of the Viewer based upon the particular needs of the VEHRS and the needs of end users. Some may be implemented to provide a complete EHR-S solution. Others may implement a Personal Health Record ("PHR") solution designed for consumers to view, add to, and use information about their own health status and issues. Some may implement the service and repair history for a family's automobiles, or simply a personalized cookbook in which each recipe is stored in a separate document that can be selectively shared with other cooks. The foregoing are examples and are not intended to limit the possible fields in which the DBKS may be implemented or the uses to which the DBKS may be addressed. The Viewer may be implemented as a thick-client software product, but it also may be implemented as components running in an industry-standard web browser, possibly using Asynchronous JavaScript and XML ("AJAX") to speed response time. There are only two real characteristics for Viewer software: that it supports a sufficient number of the services offered by the Gate Server it uses to implement an effective solution, and that its solution meets all of the various standards and requirements of the Gate Server and the entity implementing the DBKS implementation.

The name we have given to this end user device, the Viewer, implies that implementations of the Viewer provide a visual user interface, but some implementations of the Viewer may instead provide the end user software with an aural interface. This is particularly useful for the visually impaired community and for those situations where visual display devices are cumbersome or inconvenient. Such aural implementations of the Viewer are meant to be included in this and other descriptions below of the Viewer, despite the implications of the name.

Entity Summary Documents

The vast majority of documents stored in the method are about one or more entities: Patients, doctors, health provider organizations, family members, automobiles, insurance policies, chapters (of a book, which would be a separate entity), publishers, and so forth. Some implementations of the DBKS may choose to maintain a separate document, an Entity Summary Document containing the most current information describing the entity and/or the current status of key parameters of the entity such as current address, last service date, primary diagnosis, and other units of information. In such implementations, the Entity Summary Document should itself be formatted according to a published Document Standard and the information within it should conform to the published Information Standards of the implementer of the DBKS so that External Requestors can properly interpret the documents when they are received.

One of the functions of the Gate Server, in such an implementation, is to monitor all new Protected Documents accepted into the method to see if they contain any information that changes any of the information currently stored in the Entity Summary Document for the entities referred to in the Protected Document. In one implementation, if any differences are found, a copy of the then-current Entity Summary Document for the entity is made, the new information inserted into the copy and the old information removed, links added to both the source document for the new information and to the previous Entity Summary Document and then the copy marked as the new current Entity Summary Document for the entity.

In typical usage of such an implementation, a copy of the current Entity Summary Document is provided to all External Requestors working with the entity, provided this is in keeping with all Privacy and Security Standards and Authentication Standards of the DBKS implementer.

Document and Entity Maps

In order to speed processing, searching and response time, some implementations of a DBKS may elect to keep metadata about a Protected Document in a separate document. We are calling such metadata Document Maps. One possible implementation may handle a Document Map as its own document, with its own defined Information and Documents standards to which it must comply.

In various implementations, a Document Map might contain the most critical units of information in the Protected Document and/or those most likely to be used in searching for the Protected Document. The Document Map may also identify some or all of the entities described in the Protected Document. It may also be used to record relationships, such as the relationship between this Protected Document and other Protected Documents.

If the Protected Document is an Entity Summary Document, some implementations may treat the Document Map separately as an Entity Map. Entity Maps in such an implementation may be used heavily to document the relationship between the entity that is the subject of the Entity Summary Document it references and other entities in the system. The format for how these relationships are documented in the Entity Map would be specified in the Document Standard to which the Entity Map conformed.

In implementations that use Document Maps and Entity Maps, the Gate Server and External Requestors can use this metadata to speed searching and response time, as the metadata documents would be substantially smaller than the documents they represented and the information stored in such documents would typically be formatted expressly for these purposes.

Also note that in such implementations, setup, configuration, and management information needed to control the method can itself be documented in Protected Documents with their associated Document Maps and with Entity Summary Documents and their associated Entity Maps. This is so because each Viewer instance, Gate Server, Document Bank, and so forth are simply entities that have relationship to other entities. Thus we see in such implementations that all information about all entities and the relationships between them can be stored and managed with two structure primitives: documents and maps. The DBKS method may be optimized to take advantage of this architectural simplicity in order to improve responsiveness and effectiveness. Indeed, in further implementation of a DBKS described below, we provide methods for a community of inventors to contribute to this effort.

Interim Staging Layers

To improve response time to requests from External Requestors, some implementations may provide high scalability storage solutions, consisting of commonly available storage devices and software designed to rapidly store and extract information from them, under control of the Gate Server. FIG. 1 visually depicts several Interim Staging Layers and how they communicate with other components of the DBKS. In recent years, rapid advances in data storage and retrieval have been made to serve the needs of the largest web services, such as Google, Amazon, Facebook and others. Many of these high speed, high scalability solutions belong to a category called NoSQL databases (with SQL, or Structured Query Language, being the language commonly used to send and receive data from RDBMSs). These include BigTable (Google), HBase (Apache, Yahoo, Facebook), Cassandra (Facebook), the aforementioned CouchDB (Apache), SimpleDB (Amazon) and others. Some implementations of the DBKS may employ such structured storage solutions to speed response time by holding copies of the most frequently used Document and Entity Maps or to hold Protected Documents and other information expected to soon be requested by External Requestors. Depending on the requirements of some implementations there may be several Interim Staging Layers supported in a particular implementation of a DBKS. There may also be separate Interim Staging Layers dedicated to the exclusive use of specific Accelerator Applications (described below). Some implementations of Interim Staging Layers may store the information in Random Access Memory ("RAM") or solid state disk drives instead of typically slower hard disk drives.

Accelerator Applications

Figure 2:
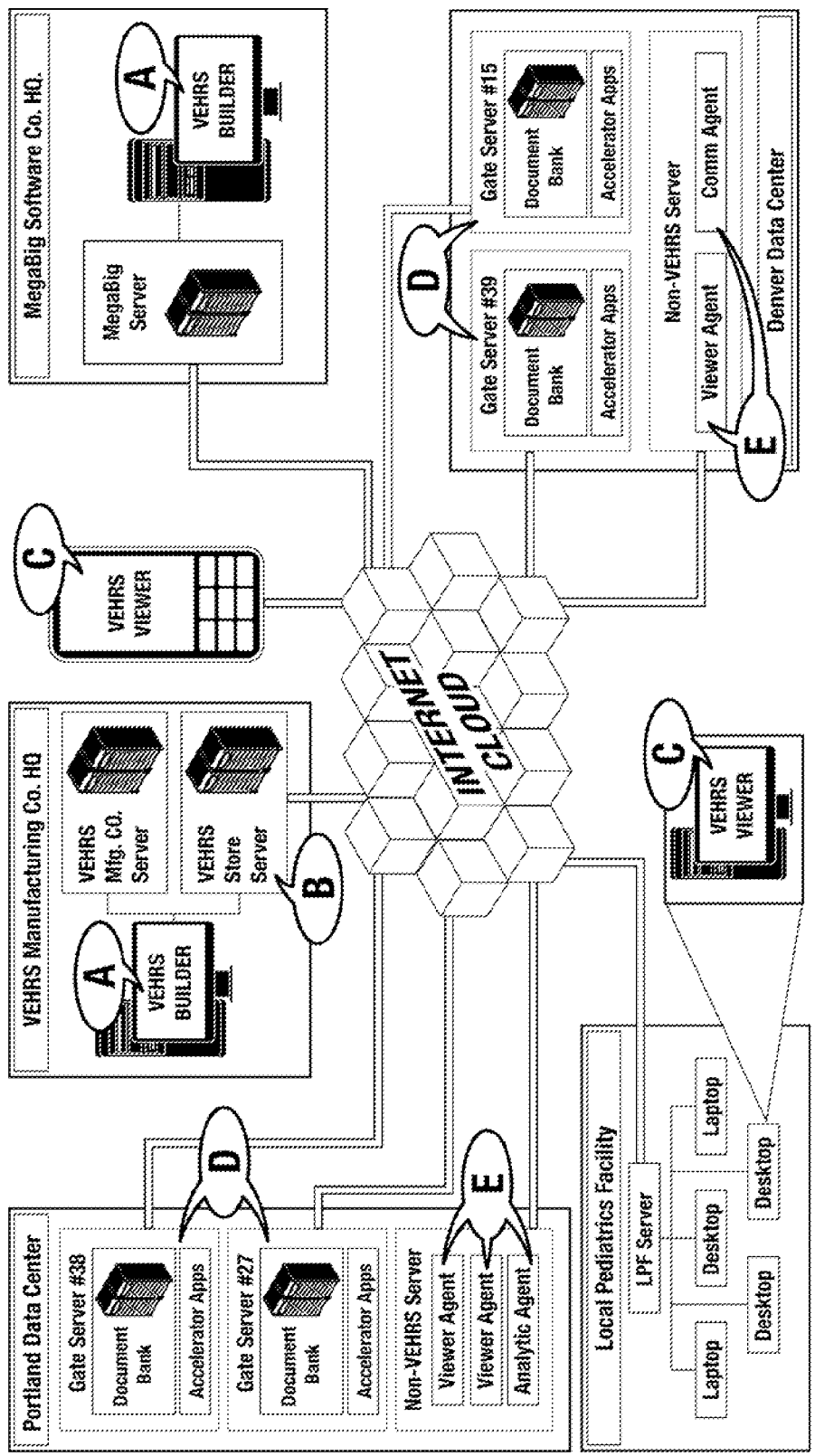
FIG. 2 is a schematic view of one embodiment of a Variable Electronic Health Record System and the Document-Based Knowledge System upon which it is built.

Some implementations of a DBKS may also provide additional software components to run under the control of the Gate Server to predict what requests for Protected Documents and other information may be received by the Gate Server in the near future and prepare such information for faster delivery to the requestor when the request is received. FIG. 1 visually depicts how Accelerator Applications work within the DBKS. FIG. 2 visually depicts Accelerator Applications in the wider VEHRS discussed below. Implementations using Interim Staging Layers may copy the Protected Documents and other information into an Interim Staging Layer for quick delivery upon request receipts. Other implementations may actually deliver selected Protected Documents and other information to the External Requestor prior to receiving a request for the information. Such implementations would need to engineer their implementations of the Viewer software, or the Data Agent software if Data Agents are implemented, in order to receive the pre-delivered information into local temporary storage and to use that information when requested by the end user instead of sending a request to the Gate Server.

Various implementations of Accelerator Applications may use different strategies for predicting what information will likely be requested in the near future. Some may track the behavior of specific end users in order to estimate the most likely next requests based on past performance. Others may track the behavior of groups of users based on the role the user performs and make predictions for what a specific user may request based on the role that user is currently performing. Others may use information about when specific users usually log on to the system, in order to have the most likely information ready to go as soon as they log in. Still other implementations may inspect the Protected Documents and other information recently requested for clues as to what will be requested next. Some implementations may use combinations or variations of all of these strategies, or other strategies not mentioned, to predict what information requests will shortly be received.

As one example, an Accelerator Application may inspect the schedule of Dr. Jones and see that she is scheduled to perform office visits with six patients from 8:00 am to Noon today and prepare to have the doctor's schedule and selected documents for each of the six patients prepared for quick delivery by 7:45 am. It might also observe that one of the patients has type II diabetes and create a trend report on the last six months HbA1c lab readings because Dr. Jones frequently has asked for such a report when seeing a patient with type II diabetes.

Data Agents

Some implementations of a DBKS may also use Data Agents for multiple purposes. FIG. 1 visually depicts several types of Data Agents in an external datacenter but running as a part of the overall method. Also see item E in FIG. 2 for a visual depiction of several types of Data Agents embedded into a VEHRS implementation. Data Agents are separate software applications (or a collection of software components that together act as an application) and which run outside of the control of the Gate Server. Thus, they are similar to Viewer instances in that they register with the Gate Server and request, receive, and use Protected Documents and other information in a similar manner to that performed by Viewer instances. They are different than Viewer instances, however, in that they have no end user interface. If they did, they would be Viewers instead of Data Agents. Their job is to do processing work and return results, and in some instances to provide temporary storage, in order to support the needs of Viewer instances, the Gate Server, Accelerator Applications, other Data Agents or, in some situations, machine processes acting outside of the control of the method. In some implementations of a DBKS, the Gate Server may provide services to Data Agents that are not supported for Viewer instances and vice versa. The particular DBKS implementation may impose restrictions on the environment in which the Data Agent may run, such as requiring Data Agents to only run in datacenters that meet or exceed a set of minimum standards.

There are few limits on what a Data Agent can do, provided that it is always in compliance with the Authentication, Document, Information and Privacy and Security Standards in effect for the implementation of a DBKS in which they are running Nevertheless, an exemplary implementation may include Data Agents to perform the following functions:

1. Viewer Agents. Data Agents may, in some implementations of a DBKS, be designed to work in conjunction with a specific Viewer instance to speed overall method response time to that instance, or for other purposes. Such a Viewer Agent may automatically be launched whenever the Viewer is launched. It may in some implementations take over some or all of the predictive modeling work of an Accelerator Application to expand the overall processing power of the system. It may also do this because it is located closer to the Viewer instance and thus able to provide greater speed improvement, such as if it was running in the end user's local datacenter or even, in some situations, on the same end user hardware that the Viewer instance is running In other situations, such as when the Viewer instance is being run in insecure environments like a hotel business center desktop or on low end devices such as smartphones or netbooks, the Viewer Agent may take over the bulk of the processing work needed to build and modify the web pages being presented to the end user.

2. Analytic Agents. In some implementations, Data Agents may be used for data aggregation and analysis and to create new documents from the results. Financial Dashboards and Disease Registries are two examples of functions that may be performed by such Analytic Agents. A large scale research study may also be performed by an Analytic Agent, or by groups of Analytic Agents working in parallel. This potential application of the present invention fulfils one of the design goals originally described above. Because all data from all patients and from all providers caring for each of those patients may be stored in a common published format, most of the current barriers to large scale research projects could be eliminated. Currently, research projects are so expensive to implement they are typically, unless government-funded, only performed by organizations that stand to benefit from the results, such as pharmaceutical companies and the largest of healthcare provider organizations. Using a DBKS that implemented Analytic Agents may substantially reduce the cost of research projects to the point where far more research projects could be implemented by far smaller organizations. The impact of the knowledge learned from such research on our individual health and the health of our families is hard to estimate, but it is likely to also be substantial. This is another way in which the present invention turns an information system into a knowledge system.

3. Communication Agents. In some implementations Data Agents may be used to communicate with machine processes that are outside of the control of the method. Indeed, in one implementation, such Communications Agents may be the only components controlled by the method that are allowed to communicate to processes not controlled by the method. Such Communications Agents may be used for different purposes in different implementations. In an implementation designed to support Family Financial applications, a Communications Agent may be used to request and receive reports from insurance, investment, and other financial services providers. In the healthcare industry, Communications Agents may be use to implement the exchange of health information with healthcare providers not using an EHR-S that is compliant with this method as well as for the submission of health information required by regulatory bodies, quality reporting agencies, public health departments and payers.

Multiple Data Agents may be in use at the same time, in various configurations. Each may be registered and launched by a Viewer instance or by the Gate Server itself, or by other mechanisms supported by the specific DBKS implementation. In addition, one Agent may be able to launch another Agent, passing along its rights and duties to the child Agent. For example, if a user saves a Clinic Visit document in the Viewer, the Viewer Agent servicing that Viewer might launch an Analytic Agent to update the current flow chart of vitals for that patient.

DBKS Conclusion

In sum, the DBKS allows multiple independent healthcare providers to work in tight real-time collaboration in caring for a patient because each provider can see the information added by the other providers caring for the patient in near-real time, since all of the documents from all of the providers are kept in the same location. It provides data resiliency because multiple copies of the documents are kept at geographically remote backup sites. It substantially lowers the cost and complexity of large scale research because all of the data is formatted in compliance to published standards. The DBKS also provides these and other benefits to other industries besides the healthcare industry.

Overview of a Variable Electronic Health Record System

In order to meet the design goal of lowering the dependence of providers on vendors, we need a way in which providers can replace parts of their EHR-S without having to replace the whole thing. The difficulty in doing so is the accessibility of the data. If a new system is installed to replace part of the task of a full system, the full-system is typically unaware of the data structures the new system uses to store its information. However, as we have seen above, this is not so if the full system and partial system both store their information in a DBKS, since the information is stored in separate documents that all comply with a set of common standards. The full system can continue to produce its Protected Documents. The new partial system can produce its new Protected Documents and both systems can read, understand and use each other's Protected Documents since they all comply with the published Information and Document Standards. Thus, to meet the design goal of lowering the dependence of providers on their vendors, we need a way for software manufacturers creating EHR-S to all use the same DBKS. We call this aspect of the present invention the Variable Electronic Health Record System.

Due to the features of the DBKS, there are several different ways in which implementers can provide a VEHRS. Some implementations may provide a set of specifications for independent software manufacturers to manufacture their own Viewers that can send and receive Protected Documents and other information to the Gate Server. Other implementations may provide a set of specifications for independent software manufacturers to produce Accelerator Applications, possibly with their own Interim Staging Layers, to work inside of and under the control of the Gate Server. Still other implementations may provide specifications for independent software manufacturers to create Data Agents that can work within the method, requesting and receiving Protected Documents and other information from the Gate Server and possibly servicing Viewers that they manufacture or Viewers from other manufactures. Some implementations of the method may go further and provide a set of specifications for independent software manufacturers to provide parts but not all of a complete Viewer implementation by breaking the complete Viewer implementation into sub-units capable of working together as a complete solution. We will describe the details of each of these possible implementations of the method. Other implementations may offer combinations of these different implementations or additional ones we have not listed.

Implementations that Specify How to Independently Manufacture Complete Viewer Applications Due to the modular nature of the DBKS, it is relatively straightforward for implementers of this method to specify a way for independent software manufacturers to manufacture their own implementation of the Viewer, whether that implementation is expressed as a visual user interface or as an aural user interface. They need to specify how to send and receive Protected Documents to and from the system, most commonly by providing the set of Web Services specifications supported by the Gate Server for use by Viewer instances. They need to provide access to the published Authentication, Privacy and Security, Information, and Document Standards enforced by their implementation. Finally, they need to provide a way for Viewer instances from each Viewer manufacturer to successfully register their instances with the Gate Server. Beyond that, the details of what end-user functionality is provided by each manufacturer's Viewer implementation can be left up to that manufacturer to determine, unless the method implementer wishes to place constraints on that as well. Most commonly, the method implementer also has a legal agreement with each independent software manufacturer creating Viewer applications to work with their Gate Servers and other method components, but this is not required for the method to work.

Once these are provided, the independent software manufacturer produces Viewer implementations that allow end users to store their Protected Documents and other implementations in the Gate Server side by side with Protected Documents and other information stored by Viewer instances from other manufacturers. Because of the capabilities of the DBKS as described above, they can receive and use all of the Protected Documents and other information about a patient or other entity, whether those Protected Documents and other information were produced by this Viewer, other Viewers from the same manufacturer, and Viewers produced by other software manufacturers. This is true because all Protected Documents and other information produced by all Viewers, regardless of manufacturer, comply with the same set of Authentication, Privacy and Security, Information, and Document Standards enforced by the Gate Server implementation of the method to which all the Viewers report.

A manufacturer, or a collection of different manufacturers, may implement an entire VEHRS with a suite of different Viewers designed for different purpose. One Viewer may be designed for pediatric office visits, another for managing a diabetes registry, another for home visits by physical therapists, another for physician office billing, and so forth. Viewers specialized for management may access and use all of the Protected Documents and other information created in these and other specialized Viewers in order to manage the entire organization.

Such a combination of specialized Viewers from different manufacturers designed for specific purposes, but all working together off of the same set of Protected Documents and other information furthers the design goal of reducing the dependence of healthcare providers on a single vendor. If a provider organization had acquired or licensed a suite of Viewers from one manufacturer to implement their core EHR-S, but didn't like the Viewer that supported diabetic office visits, they may use a diabetes office visit Viewer from a different manufacturer without disrupting any of the other Viewers in use by the provider organization, and without the permission or assistance of the vendor from whom they acquired their core EHR-S.

This functionality of having multiple different specialized Viewers from many different manufacturers that all work together for a more general purpose, may be used in other industries besides healthcare. Financial services, publishing, automobile servicing, and other industries may all take advantage of this method. Specialized Viewers may even be embedded into machine tools from different manufacturers each reporting their activities with different types of Protected Documents. Management may then use Viewers specialized for machine shop management to monitor and manage all of the machine tools in the shop. In such an environment, other Viewers specialized in inventory management may be used in the tool crib and have access to the production reports from all of the various machine tools on the floor in order to predict future tooling needs. By using a DBKS that stores information in discrete documents that conform to published information and document standards any industry may break down its end user software functionality into discrete units implemented by different Viewers from different manufacturers that all work together off of a common pool of Protected Documents.

Implementations that Specify How to Independently Manufacture Accelerator Applications Some implementations of the method may provide a set of specifications and other support to allow independent software manufacturers to produce their own Accelerator Applications, possibly using their own Interim Staging Layers, for operation on the computer equipment controlled by the Gate Server and under the control of the Gate Server. Such implementations provide the software manufacturer with specifications for what technologies the Accelerator Application would need to be implemented with and specifications for an application programming interface ("API") between the Gate Server and the Accelerator Application. If an Interim Staging Layer is also being installed, the method implementer may specify the acceptable Interim Staging Layer technologies and possibly an API for the Gate Server to independently communicate with the Interim Staging Layer. Included in such APIs, the method implementer also specifies how the Accelerator Application can access the Authentication, Privacy and Security, Information, and Document Standards enforced by the method implementation. The software manufacturer produces the Accelerator Application and, if applicable, the Interim Staging Layer, and provides such to the method implementer who installs them on the method's computing equipment to run under the control of the Gate Server.

Some implementations of the method may instead prefer that acceleration technology from independent software manufacturers be implemented on computing equipment not controlled by the method. In such cases, the methodology of the present invention considers those solutions to be Data Agents, even if the method implementer provides a separate API for such accelerator Data Agents from the API specified for other Data Agents.

By providing independent software manufacturers the ability to manufacture and market Accelerator Applications and/or accelerator Data Agents, the method implementer provides an opportunity for a community of inventors to create innovate solutions to the system response time problem discussed above. It also provides this community of inventors the ability to create accelerator technology customized for the purpose of specific industries or uses. The most effective acceleration technology may require intimate domain knowledge about the purpose to which the accelerated response is being delivered. For example, the acceleration algorithms that provide the fastest response time for the machining industry may not be the same as the acceleration algorithms that provide the fastest response times for the publishing industry. It is for this reason that the method recommends that method implementers provide support for multiple Accelerator Applications to run under control of the Gate Server for different purposes, though this is not a requirement for the method.

The fastest acceleration technology may be achieved by combining Accelerator Applications with temporary storage technology to hold interim results and for holding Protected Documents and other information prepared for fast delivery to end users. To this end, optional separate Interim Staging Layers optimized for individual Accelerator Applications may be used.

Implementations that Specify How to Independently Manufacture Data Agents

Some implementations of the method may also allow independent software manufacturers to produce Data Agents that can participate in the method for multiple purposes. Similar to the needs of independently manufactured end user Viewers, the method implementer may provide specifications for how independently manufactured Data Agents send and receive Protected Documents and other information to and from the system, how they access to the published Authentication, Privacy and Security, Information, and Document Standards enforced by the implementation, and how the Data Agent instances successfully register with the method. The method implementer may also specify what types of Data Agents their implementation of the method supports and provide specialized APIs for each of the supported Data Agent Types. The previously described Viewer, Analytic, and Communication Agents may be among those supported by specific implementations of the method in addition to other Data Agent types not described herein.

Implementations that Specify How to Independently Manufacture Sub-Units of a Complete Viewer Application Beyond the various implementations described above, by which independent software manufacturers may produce separate software applications, be they Viewers, Accelerator Applications, or Data Agents, that can work in concert together, some method implementers may also provide specifications for how independent software manufacturers may produce sub-units of a complete Viewer solution, such that the sub-units work together to provide a complete Viewer solution. Such a solution provides end users with even finer grain control of their knowledge system than possible if the complete Viewer has to be replaced to take advantage of innovative solutions from a different manufacturer. Some examples of such fine-grain control will be discussed after we outline one possible way in which such Viewer sub-units may be defined and supported by the method implementer.

To support the ability for independent software manufacturers to produce sub-units of a complete Viewer solution, method implementers may specify what types of sub-units are supported and provide a framework and set of specifications in which the supported sub-units may work together as a complete Viewer solution. One possible implementation, but by no means the only possible implementation, is described below.

One Exemplary Implementation of a Viewer with Nested Sub-Units

Figure 3:
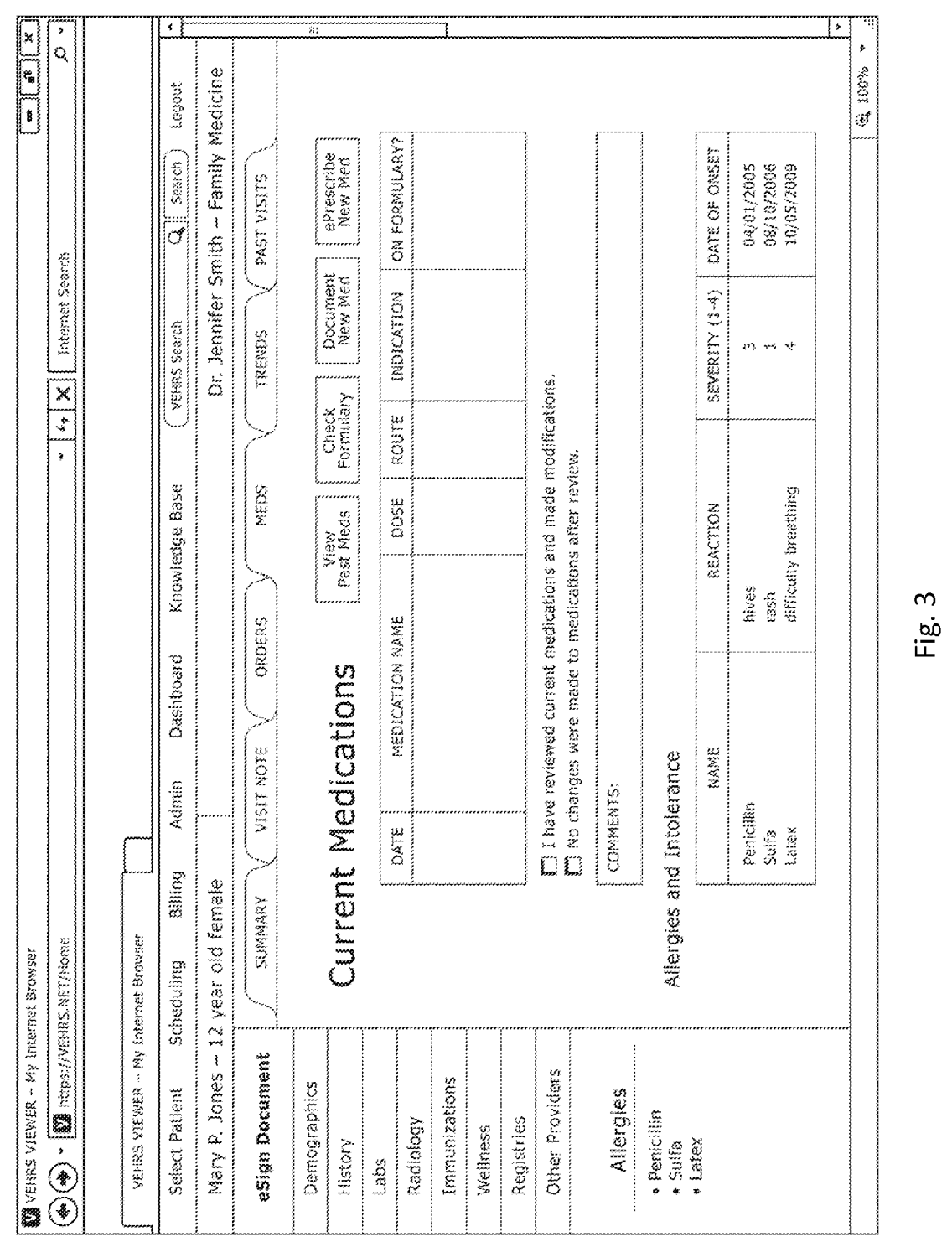
Figure 4:
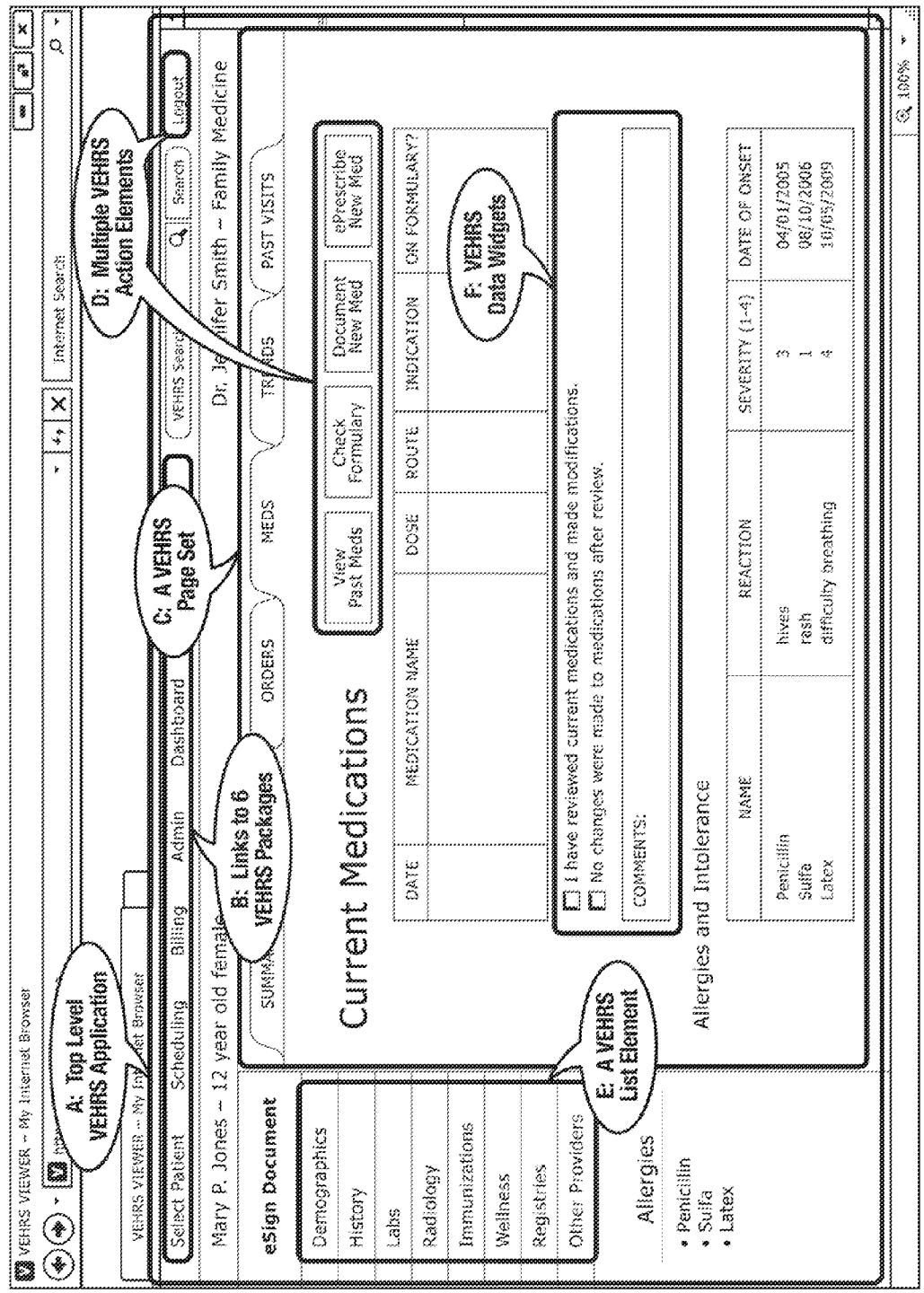
FIG. 4 is a view of a display screen for an exemplary embodiment of the end user software of a Variable Electronic Health Record System showing some portions of the display that may be varied.

In this exemplary implementation, the method implementer provides support for both a set of sub-unit primitives and a set of nested sub-units, each of which contain other sub-units and some of which can themselves be contained in other nested sub-units. It is described with a visual user interface, but other implementations may provide similar functionality with an aural user interface. To aid the reader in interpreting the following discussion, two figures are provided. FIG. 3 presents a possible implementation of a common EHR-S screen using VEHRS technology. FIG. 4 shows the same screen with some of the nested sub-units described below identified.

Supported Sub-unit Primitives

This exemplary implementation supports the following sub-unit primitives:
1. Logic Elements. Logic Elements, in this exemplary implementation, may come in several varieties and be used in several different situations. Some Logic Elements may include compiled functions (small executable programs) that are provided by either the method implementer or other software manufacturers. Other Logic Elements may be interpreted software code evaluated at run time. Logic Elements in this implementation are the only sub-units that do not have a presence on the user display. Instead, the method implementer may specify how Logic Elements may be embedded into or called from other sub-units of the complete Viewer solution.
2. Display Elements. Display Elements, in this exemplary implementation, are elements that display on the user display device or in printed output. Text of various fonts and backgrounds, pictures, graphs, and other visual elements may be displayed on the screen or printed output using Display Elements. Display Elements typically do not perform any action or accept any input. Display Elements most typically have an area of the display screen for which they are responsible for painting during screen refreshes.
3. Data Widgets. Data Widgets, in this exemplary implementation, are software components that allow data to be entered via some data input device, such as a keyboard, a mouse, a microphone, and so on. See item F on FIG. 4 for a visual depiction of several Data Widgets. Data Widgets may also be configured to accept data input from an electronic data input device. Each Data Widget may specify a data type and a data input location on the screen. In addition, the Data Widget may specify several parameters, indicating the associated logic to be used with the Widget. These parameters may identify specific Logic Elements to be run or called by the Data Widget at specific times, such as a Pre-Edit Authorization Logic Element, a Post-Edit Validation Logic Element, and an On Edit Logic Element. Each of these Logic Elements is defined by the method implementer or other software manufacturer and is triggered by the Data Widget at the indicated time (Pre-Edit, Post Edit, etc.). Data Widgets may also be implemented in a read-only mode that does not allow the data to be altered. This mode may be used, for example, when the information displayed is historical information or when the user does not have sufficient rights according to the Authentication or Privacy and Security Standards enforced by the method to change the information. Data Widgets also typically have an area of the display screen for which they were responsible.

Supported Nested Sub-units

This exemplary implementation may support the following nested sub-units:
4. Action Elements. Action Elements, in this exemplary implementation, are components designed to perform some preconfigured action when selected. See item D on FIG. 4 for a visual depiction on several Action Elements.

Action Elements are typically displayed on the screen and perform their defined task when activated by the user via mouse click, Hot Key, spoken keyword, etc. For some Action Elements the defined action may be to snap a reading from an attached electronic data input device. But more typically, clicking or otherwise selecting an Action Element may trigger a pre-selected Logic Element or activate another Viewer sub-unit currently authorized for this user session. An Action Element may have the following attributes: default Height & Width, Small Icon, Large Icon, Background, Display Text and font, Down Arrow Menu Items, Relative or absolute order in a collection of Action Elements. Action Elements may be provided by the method implementer or acquired from other sources. For example, a manufacturer of automated data collection equipment may include instructions for downloading an Action Element that triggers their equipment. Action Elements also typically have an area of the display screen for which they were responsible.

5. List Elements. List Elements, in this exemplary implementation, are user interface elements that have responsibility for an area of the Viewer screen and contain a grouping of other Viewer sub-units. See item E on FIG. 4 for a visual depiction of a List Element containing multiple Action Elements. For example, a vertical or horizontal menu may be implemented by a List Element containing a group of Action Elements. In another example, a List Element may implement a table of information by containing a group of Data Widgets. List Elements may also contain other List Elements. In the previous example, the table of information may be implemented by a List Elements that contains other List Elements arranged vertically to display the different rows of the table. Each of those List Elements then contains a collection of Data Widgets or Display Elements to implement the various columns of the row.

6. Page Definitions. Page Definitions, as in this exemplary implementation, may provide a specification for how to display on screen (or on printed output) some of the data stored in a Protected Document of a specific Document Type. This data may be rendered on screen or on printed output via a collection of sub-units defined for the Page Definition. Display Elements, Data Widgets, Action Elements and List Elements may be used in various configurations to render the portion of the assigned Protected Document. Logic Elements may also be attached to Page Definitions, in order to perform specified logic algorithms in defined circumstances. Each Page Definition may only specify one implementation of rendering the data visible to the user. For example, for documents of the same Document Type, there may be a one Page Definition for displaying the assigned portion of the document on a full sized computer monitor, a collection of separate Page Definitions for displaying the same information on the typically smaller screen of a tablet computer or smartphone, and other Page Definitions for rendering the same information on printed output. The right to use the Page Definition to view the data may be controlled by the rights associated with the data itself or by rights associated with the current user, as specified by the current Authentication or Privacy and Security Standards enforced by the method. In this exemplary implementation, a Page Definition would be contained in a Page Set, as described below. This is so that the integrity and security of the complete Protected Document can be preserved. However, other implementations of the method may implement this functionality in other ways. The user's rights to edit the data, or other system parameters, such as the default font to use, may be passed down to the Page Definition by the Page Set that contains the Page Description. The Page Definition, in turn typically passes these rights and other parameters down to the nested Data Widgets, Action Elements and other sub-units contained in the Page Definition.

7. Page Sets. A Page Set, in this exemplary implementation, is a group of Page Definitions for use with a specific document type. See item C on FIG. 4 for a visual depiction of a Page Set. When a new document is created, a Page Set may be used to display the information and collect the data from the user. Typically, every Page Set may have at least two Page Definitions, one for displaying the data on screen and accepting user input and another for printing. A Page Set may implement support for a specific Document Type by spreading the data input and display over multiple Page Definitions (e.g. multiple screens). Each Page Definition may collect and display only a portion of the information in the document. Saving a document may be carried out at the Page Set level, independent of which Page Definition was used to input the data. Page Sets can have Logic Elements associated with them, such as an Authorization To Edit Logic Element or a Validation Logic Element to ensure that the entire document controlled by the Page Set is in compliance with the Document Standards enforced by the method for that document type. These Logic Elements may allow special logic to be added for specific Document types. A Page Set typically has responsibility for a specific area of the display screen. It usually passes a smaller screen area down to the active Page Definition for it to control when that Page Definition is activated. The currently active Page Set typically controls a larger portion of the display screen than the other active Action Elements, List Elements, Display Elements and Data Widgets currently displayed, because the Page Set is the sub-unit that displays the active Protected Document to the user and in which the user typically performs data input. However, this may not always be the case.

8. Solution Sets. Solution Sets, in this exemplary implementation, are collections of Page Sets, List Elements, Action Elements, Display Elements, Data Widgets and Logic Elements for logic that needs to be performed at the Solution Set level. Solution Set can also contain other Solution Sets. Solution Sets typically control a large area of the display screen when they are active. Solution Sets in this implementation are designed to meet a specific business purpose, such as a Pediatric Office Visit or an Endoscopy Procedure. This may involve using one or more List Elements containing Action Elements to provide a menu of available options to the user along with a Page Set to display the currently active Protected Document.

9. Packages & Applications. VEHRS Packages, in this exemplary implementation, are a collection of Solution Sets and other sub-units designed to implement a common functionality. See item B on FIG. 4 for a visual depiction of links to several VEHRS Packages, which are implemented by a set of Action Elements (Select Patient, Scheduling, etc.) embedded in a List Element. When any of these Action Elements are clicked on, the associated VEHRS Package is displayed. Currently the Clinical Package is displayed on the screen depicted in FIG. 4. VEHRS Applications are a collection of VEHRS Packages designed to implement a complete Viewer solution. See item A of FIG. 4 for a depiction of a complete VEHRS Application. In this implementation only one VEHRS Application can be active at a time in the same browser window. Other browser windows may display other VEHRS Applications. A VEHRS Application may be equivalent to an entire traditional EHR-S software program, whereas a VEHRS Package may be equivalent to a module within a traditional EHR-S program. For example, separate Clinical and Billing Modules in a traditional EHR-S may be implemented in VEHRS via Packages—a Clinical Package and a Billing Package.

Benefits of a Viewer Implemented with Nested Sub-Units

By allowing a complete Viewer solution to be implemented as a collection of nested sub-units, potentially available from multiple independent software manufacturers, the method implementer may allow end users of their implementation to have fine-grained control over how their complete EHR-S or other software solution behaves. For example, a healthcare provider organization may acquire the rights to use a Viewer implementation from a large health IT vendor that consisted of a complete VEHRS Application, with multiple nested VEHRS Packages, hundreds of nested VEHRS Solution Set and thousands of nested Page Sets, List Elements, Logic Elements, Action Elements, Display Elements and Data Widgets. The healthcare provider organization may implement this complete Viewer solution and find that most of their users were satisfied with the solution. However, typically when this is done, there are a handful of situations where the overall complete solution that is best for the larger organization doesn't work for specific needs within the organization. These may be large needs such as Billing. The clinical functionality of the system may be ideal for medical staff, but if the billing package was inadequate for the billing office, it may acquire a separate VEHRS Billing Package from a vendor that specializes in healthcare billing functionality. Alternatively, the dissatisfaction may be in a small area. Perhaps the Office Visit Solution Set contained Page Sets for pediatric office visits that weren't satisfactory for children with eating disorders. In this situation, an energetic pediatrician might research the market of available Page Sets and find a Pediatric Office Visit Page Set produced by a non-profit organization that specialized in eating disorders. With a Viewer implementation using nested sub-units as described above, the healthcare provider organization may acquire that Page Set and insert it into their Viewer implementation without disrupting any of the other users of the complete Viewer solution. The data from this new Page Set may be stored in a Protected Document of a different type than the Page Set it replaced (or possibly not, depending on the source of the dissatisfaction with the previous Page Set), but this new Protected Document still conforms to the Information and Document Standards enforced by the general method implementation and thus the Logic Elements, Solution Sets, Action Elements, and other sub-units of the complete Viewer solution, as well as the other Data Agents and Accelerator Applications active for the organizations solution, may still read, extract, understand, and act on the units of information contained in the Protected Document created by the new Page Set.

This level of fine-grained control by providers over the EHR-S and other health IT software used by the healthcare industry may have a profound effect on the ability of each healthcare provider to provide the best care possible to their patients. It may spawn a wave of innovators to develop and implement creative new care protocols, because they have a way to quickly and relatively inexpensively create new Page Sets and other sub-units to implement and document those new care protocols without disrupting the rest of the organization they work for.

There are two other components an implementer of the method may provide to end users to further enhance the effectiveness of a Viewer implemented as nested sub-units: a Builder application that may accomplish the substitution of the new Page Set for the old Page Set in an automated and orderly manner, and an Online Store to provide a central place for manufacturers of new Page Sets and other sub-units and end users looking for such sub-units to replace sub-units they were dissatisfied with, to meet and do business. We will now describe these two variations.

The VEHRS Builder

In some exemplary implementations of the method, the implementer may offer an application, which we will call the VEHRS Builder, which allows the end users of a Viewer implemented with nested sub-units to replace sub-units in a specific Viewer instance with different sub-units of the user's preference, provided they had the rights to do so. See item A on FIG. 2 for a visual depiction of the VEHRS Builder. Some implementations of a VEHRS Builder may also allow the end user, with appropriate rights, to edit existing page-sets or other sub-units of the complete Viewer solution. Further variations of this implementation may allow users to create new Page Sets and other sub-units of a complete Viewer solution. This variation may have the effect of lowering the health IT cost for the entire healthcare industry, because it allows even the largest HIT vendors to implement complete Viewer solutions using relatively inexpensive commercial off-the-shelf software. A similar effect may be available in other industries.

The VEHRS Online Store

Some implementations of the method may also host an online marketplace, which we will call the VEHRS Online Store, to allow independent software manufacturers of VEHRS Page Sets, Solution Sets, Packages and entire VEHRS Applications, as well as other sub-units of a complete Viewer solution, to market their method components to end users and end user organizations. See item B in FIG. 2 for a visual depiction of the VEHRS Online Store. Such a VEHRS Online Store may streamline the process of improving each end user's satisfaction with their Viewer solution by allowing them to quickly acquire desired sub-units.

These two variations, the VEHRS Builder and the VEHRS Online Store, may in concert lower the entry bar for producing and distributing sub-units of a complete Viewer solution. With these in place, larger healthcare providers may themselves create innovative solutions to specific issues and easily market them to end users. Currently only the very largest healthcare providers have the resources to produce their own health IT software. With the VEHRS Builder and VEHRS Online Store in place, a 20-physician clinic may have sufficient resources to build and market the VEHRS sub-units necessary to implement an innovative care protocol. By doing so, they may be able to add a profit-center to their organization and build brand recognition and reputation for their clinic. Similarly, non-profit organizations dedicated to specific disease states or professional organizations dedicated to a specific profession, may develop and offer at no-charge on the VEHRS Online Store (if this was supported by the method implementer) open source sub-units of a complete Viewer solution that they build with the VEHRS Builder. These variations provide an additional way in which the present invention meets the design goal of lowering the dependence of healthcare providers on the vendors of their EHR-S and other Health IT software. Similar benefits would be available for other industries.

Benefits of a Variable Electronic Health Record System

By providing some or all these variations by which independent software manufacturers can produce and market their own Viewers, Accelerator Applications, Interim Staging Layers, and Data Agents, the method implementer enables a wide community of inventors to compete with each other in providing the best overall solution to the customer's needs or in providing specific solutions for specific purposes or specific user populations, while still having all of the information produced by these various elements understandable and usable by each of the solutions because that information is stored in discrete units that all conform to the published Authentication, Privacy & Security, Information, and Documents standards enforced by the method. Thus, in one method, we provide a way for large information technology companies to marshal their money power to produce the best overall solutions for large organizations or user populations while still allowing small inventors a way to provide innovative new solutions or to provide solutions for specific purposes or user populations that are not well served by the large overall solutions. This is one more reason we label this method a system for generating knowledge and not just information.

We have collectively named these various implementations the Variable Electronic Health Record System because it was originally designed to meet the pressing needs of the healthcare industry. However, readers familiar with the technology will easily see how the method can be used to produce variable solutions for almost any industry or user population.

CONCLUSION

While the above pages describe the detail of some exemplary implementations of a DBKS and a VEHRS built on the foundation provided by a DBKS, these implementations are not limiting and are not necessarily exclusive of each other, and it is contemplated that particular features of various embodiments may be omitted or combined for use with features of other embodiments while remaining within the scope of the invention.

I claim:

1. A method for managing information from multiple separately authored electronic documents comprising the steps of:
   (a) Providing a set of one or more document standards;
   (b) Providing a set of one or more information standards;
   (c) Providing a set of one or more authentication standards;
   (d) Providing a set of one or more privacy and security standards;
   (e) Storing electronic documents into a document bank consisting of one or more electronically accessible electronic data storage devices;
   (f) Providing gate server software that performs the following server processes, the processes executed on a processor:
      (i) Authenticating user entities as authenticated entities;
      (ii) Validating prior to transmission that the transmission of each electronic document and other information to an authenticated entity complies with the privacy and security standards and the authentication standards;
      (iii) Validating that each unit of information complies with the information standards prior to the storage, control, or use thereof;
      (iv) Validating that each electronic document complies with the document standards before the storage, control, and use thereof;
      (v) Creating new electronic documents;
      (vi) Receiving and fulfilling, partially fulfilling, or rejecting requests from authenticated entities for documents and other information in accordance with the privacy and security standards and the authentication standards;
   (g) Providing one or more end user software components for use in end-user computer processors in order to establish communications sessions with authenticated entities controlling the end user computer processors that comply with the authentication, privacy and security, document, and information standards;
   (h) wherein gate server processes validate an entity controlling end user software components in accordance with the authentication standards before delivering information to or accepting any information from the end user software component;
   (i) wherein no information is delivered to an authenticated entity until the gate server processes have determined that the delivery of such information to the authenticated entity at a point in time in question complies with the privacy and security standards;
   (j) wherein the method is the primary mechanism used by the authenticated entities sending information via the method for storage of that information;
   (k) wherein the gate server processes control access to the electronic documents in the document bank;
   (l) wherein only electronic documents and other information that comply with the information standards and the document standards are permanently stored in the document bank; and
   (m) wherein new information is created by the gate server processes.

2. The method of claim 1, further comprising the steps of:
   (a) Providing one or more accelerator applications running on computer processing equipment controlled by a gate server that are under the control of the gate server software;
   (b) wherein the accelerator applications predict what documents or other information under the control of the gate server software will be requested by individual authenticated entities; and
   (c) wherein the accelerator applications prepare the predicted documents or other information for delivery to the authenticated entity.

3. The method of claim 2, further comprising the steps of providing specifications for how independent software manufacturers can manufacture end user software that can establish communications sessions with the gate server in conformance with the authentication, privacy and security, document, and information standards provided by the method.

4. The method of claim 3, further comprising the steps of providing specifications for how independent software manufacturers can manufacture accelerator applications.

5. The method of claim 4, further comprising the steps of providing specifications for independent software manufacturers to manufacture sub-units of an end user software solution.

6. The method of claim 5, wherein:
   (a) The information sent and received to and from authenticated entities is restricted to health information and other information used in delivering healthcare services or related thereto; and
   (b) The entities authenticated for participating in the method are healthcare providers, healthcare provider organizations, patients and the authorized representatives of these entities.

7. The method of claim 1, further comprising the steps of providing specifications for how independent software manufacturers can manufacture end user software that can establish communications sessions with a gate server in conformance with the authentication, privacy and security, document, and information standards provided by the method.

8. The method of claim 7, further comprising the steps of providing specifications for independent software manufacturers to manufacture sub-units of an end user software solution.

9. The method of claim 8, wherein:
 (a) The information sent and received to and from authenticated entities is restricted to health information and other information used in delivering healthcare services or related thereto; and
 (b) The entities authenticated for participating in the method are healthcare providers, healthcare provider organizations, patients and the authorized representatives of these entities.

10. The method of claim 1, wherein:
 (a) The information sent and received to and from authenticated entities is restricted to health information and other information used in delivering healthcare services or related thereto; and
 (b) The entities authenticated for participating in the method are healthcare providers, healthcare provider organizations, patients and the authorized representatives of these entities.

11. The method of claim 2, wherein:
 (a) The information sent and received to and from authenticated entities is restricted to health information and other information used in delivering healthcare services or related thereto; and
 (b) The entities authenticated for participating in the method are healthcare providers, healthcare provider organizations, patients and the authorized representatives of these entities.

12. The method of claim 3, wherein:
 (a) The information sent and received to and from authenticated entities is restricted to health information and other information used in delivering healthcare services or related thereto; and
 (b) The entities authenticated for participating in the method are healthcare providers, healthcare provider organizations, patients and the authorized representatives of these entities.

13. The method of claim 4, wherein:
 (a) The information sent and received to and from authenticated entities is restricted to health information and other information used in delivering healthcare services or related thereto; and
 (b) The entities authenticated for participating in the method are healthcare providers, healthcare provider organizations, patients and the authorized representatives of these entities.

14. The method of claim 7, wherein:
 (a) The information sent and received to and from authenticated entities is restricted to health information and other information used in delivering healthcare services or related thereto; and
 (b) The entities authenticated for participating in the method are healthcare providers, healthcare provider organizations, patients and the authorized representatives of these entities.

15. A method for combining and synthesizing information from multiple separately authored electronic documents and delivering information to approved recipients that contains both units of information from previously existing electronic documents controlled by the method and new units of information calculated or otherwise derived from the units of information in the previously existing electronic documents controlled by the method, such method comprising the steps of:
 (a) Providing a set of one or more document standards that each electronic document must comply with;
 (b) Providing a set of one or more information standards that individual units of information must comply with;
 (c) Providing a set of one or more authentication standards to determine whether an entity is an authenticated entity;
 (d) Providing a set of one or more privacy and security standards for determining which entities can receive information and what information each entity can receive at specific points in time;
 (e) Storing electronic documents in a document bank consisting of one or more electronically accessible electronic data storage devices in such a manner that the electronic documents can be accurately reproduced;
 (f) Providing gate server software including one or more software programs or modules that are run on network computer processors which together perform the following server processes:
  (i) Authenticating an identity and user rights of any entity attempting to use the method to send or receive electronic documents or other information before establishing a communications session with that entity;
  (ii) Validating prior to transmission that the transmission of each electronic document and other information to a specific authenticated entity is in compliance with the privacy and security standards and the authentication standards;
  (iii) Validating that each unit of information is in compliance with the information standards before accepting the information for storage, control, and use by the method;
  (iv) Validating that each electronic document is in compliance with the document standards before accepting the electronic document for storage, control, and use by the method;
  (v) Creating new electronic documents for storage, control, and use by the method by combining and synthesizing information from electronic documents or other information controlled by the method and by calculating or otherwise deriving new information from the existing information and electronic documents controlled by the method;
  (vi) Receiving, fulfilling, partially fulfilling or rejecting requests from authenticated entities for electronic documents and other information in accordance with the privacy and security standards and the authentication standards;
 (g) Providing one or more end user software components to run, be displayed, or played on end-user controlled computer processors in order to establish communications sessions with authenticated entities controlling the end-user controlled computer processors that are in compliance with the authentication, privacy and security, document, and information standards;
 (h) wherein before delivering any information to or accepting any information from end user software, the gate server processes authenticate the entity controlling the end user software in accordance with the authentication standards;

(i) wherein no information is delivered to an authenticated entity until gate server processes have successfully determined that the delivery of such information to the authenticated entity at a point in time in question is in compliance with the privacy and security standards;

(j) wherein the method is the primary mechanism used by the authenticated entities sending information via the method for storage of that information;

(k) wherein the gate server processes control access to the electronic documents in the document bank and to other information stored by the method for temporary purposes;

(l) wherein only electronic documents and other information that comply with the information standards and the document standards are permanently stored in the document bank; and (m) wherein new electronic documents are created by gate server processes that combine units of information from one or more electronic documents controlled by the method, other information controlled by the method, and new units of information calculated or otherwise derived from information or electronic documents controlled by the method.

16. The method of claim 15, further comprising the steps of:

(a) Providing one or more accelerator applications that are software programs, components or modules under the control of the gate server software running on network computer processing equipment controlled by a gate server for the purpose of accelerating the response time of the method to requests from authenticated entities for electronic documents or other information;

(b) wherein the accelerator applications predict what documents or other information under the control of the gate server will be requested by individual authenticated entities participating in the method; and (c) wherein the accelerator applications prepare the predicted documents or information for delivery to the authenticated entity prior to the receipt of a request for the predicted documents or information from the authenticated entity.

17. The method of claim 16, further comprising the step of providing specifications for how independent software manufacturers can manufacture end user software that can establish communications sessions with the gate server in conformance with the authentication, privacy and security, document, and information standards provided by the method.

18. The method of claim 17, further comprising the steps of providing specifications for how independent software manufacturers can manufacture accelerator applications.

19. The method of claim 18, further comprising the steps of:

(a) Providing specifications for how a complete end user software solution that allows an authenticated user to participate in the method can be divided into a set of defined sub-units, each of which perform some of the functions of a complete end user software solution; and (b) Providing specifications for independent software manufacturers to manufacture one or more of the defined sub-units of a complete end user software solution.

20. The method of claim 19, wherein:

(a) The information sent and received via the method by authenticated entities is restricted to health information and other information used in delivering healthcare services or related thereto; and (b) The entities authenticated for participating in the method are healthcare providers, healthcare provider organizations, patients and the authorized representatives of these entities.

21. The method of claim 15, further comprising the step of providing specifications for how independent software manufacturers can manufacture end user software that can establish communications sessions with a gate server in conformance with the authentication, privacy and security, document, and information standards provided by the method.

22. The method of claim 21, further comprising the steps of:

(a) Providing specifications for how a complete end user software solution that allows an authenticated user to participate in the method can be divided into a set of defined sub-units, each of which perform some of the functions of a complete end user software solution; and (b) Providing specifications for independent software manufacturers to manufacture one or more of the defined sub-units of a complete end user software solution.

23. The method of claim 22, wherein:

(a) The information sent and received via the method by authenticated entities is restricted to health information and other information used in delivering healthcare services or related thereto; and (b) The entities authenticated for participating in the method are healthcare providers, healthcare provider organizations, patients and the authorized representatives of these entities.

24. The method of claim 15, wherein:

(a) The information sent and received via the method by authenticated entities is restricted to health information and other information used in delivering healthcare services or related thereto; and (b) The entities authenticated for participating in the method are healthcare providers, healthcare provider organizations, patients and the authorized representatives of these entities.

25. The method of claim 16, wherein:

(a) The information sent and received via the method by authenticated entities is restricted to health information and other information used in delivering healthcare services or related thereto; and (b) The entities authenticated for participating in the method are healthcare providers, healthcare provider organizations, patients and the authorized representatives of these entities.

26. The method of claim 17, wherein:

(a) The information sent and received via the method by authenticated entities is restricted to health information and other information used in delivering healthcare services or related thereto; and (b) The entities authenticated for participating in the method are healthcare providers, healthcare provider organizations, patients and the authorized representatives of these entities.

27. The method of claim 18, wherein:

(a) The information sent and received via the method by authenticated entities is restricted to health information and other information used in delivering healthcare services or related thereto; and (b) The entities authenticated for participating in the method are healthcare providers, healthcare provider organizations, patients and the authorized representatives of these entities.

28. The method of claim 21, wherein:
(a) The information sent and received via the method by authenticated entities is restricted to health information and other information used in delivering healthcare services or related thereto; and
(b) The entities authenticated for participating in the method are healthcare providers, healthcare provider organizations, patients and the authorized representatives of these entities.

29. A method for combining and synthesizing information from multiple separately authored electronic documents and delivering information to approved recipients that contains both units of information from previously existing electronic documents controlled by the method and new units of information calculated or otherwise derived from the units of information in the previously existing electronic documents controlled by the method, such method comprising the steps of:
(a) Providing a set of one or more document standards that each electronic document must comply with;
(b) Providing a set of one or more information standards that individual units of information must comply with;
(c) Providing a set of one or more authentication standards to determine whether an entity is an authenticated entity;
(d) Providing a set of one or more privacy and security standards for determining which entities can receive information and what information each entity can receive at specific points in time;
(e) Storing electronic documents in a document bank consisting of one or more electronically accessible electronic data storage devices in such a manner that the electronic documents can be accurately reproduced;
(f) Providing gate server software including one or more software programs or modules that are run on network computer processors which together perform the following server processes:
 (i) Authenticating an identity and user rights of any entity attempting to use the method to send or receive electronic documents or other information before establishing a communications session with that entity;
 (ii) Validating prior to transmission that the transmission of each electronic document and other information to a specific authenticated entity is in compliance with the privacy and security standards and the authentication standards;
 (iii) Validating that each unit of information is in compliance with the information standards before accepting the information for storage, control, and use by the method;
 (iv) Validating that each electronic document is in compliance with the document standards before accepting the electronic document for storage, control, and use by the method;
 (v) Creating new electronic documents for storage, control, and use by the method by combining and synthesizing information from electronic documents or other information controlled by the method and by calculating or otherwise deriving new information from the existing information and electronic documents controlled by the method;
 (vi) Receiving, fulfilling, partially fulfilling or rejecting requests from authenticated entities for electronic documents and other information in accordance with the privacy and security standards and the authentication standards;
(g) Providing one or more end user software components to run, be displayed, or played on end-user controlled computer processors in order to establish communications sessions with authenticated entities controlling the end-user controlled computer processors that are in compliance with the authentication, privacy and security, document, and information standards;
(h) Providing one or more accelerator applications that are software programs, components or modules under the control of the gate server software running on network computer processing equipment controlled by a gate server for the purpose of accelerating the response time of the method to requests from authenticated entities for electronic documents or other information;
(i) Providing specifications for how independent software manufacturers can manufacture end user software that can establish communications sessions with the gate server in conformance with the authentication, privacy and security, document, and information standards provided by the method;
(j) Providing specifications for how independent software manufacturers can manufacture accelerator applications;
(k) Providing specifications for how a complete end user software solution that allows an authenticated user to participate in the method can be divided into a set of defined sub-units, each of which perform some of the functions of a complete end user software solution;
(l) Providing specifications for independent software manufacturers to manufacture one or more of the defined sub-units of a complete end user software solution;
(m) wherein before delivering any information to or accepting any information from end user software, the gate server processes authenticate the entity controlling the end user software in accordance with the authentication standards;
(n) wherein no information is delivered to an authenticated entity until gate server processes have successfully determined that the delivery of such information to the authenticated entity at a point in time in question is in compliance with the privacy and security standards;
(o) wherein the method is the primary mechanism used by the authenticated entities sending information via the method for storage of that information;
(p) wherein the gate server processes control access to the electronic documents in the document bank and to other information stored by the method for temporary purposes;
(q) wherein only electronic documents and other information that comply with the information standards and the document standards are permanently stored in the document bank;
(r) wherein new electronic documents are created by gate server processes that combine units of information from one or more electronic documents controlled by the method, other information controlled by the method, and new units of information calculated or otherwise derived from information or electronic documents controlled by the method;
(s) wherein the accelerator applications predict what electronic documents or other information under the control of a gate server will be requested by individual authenticated entities participating in the method;
(t) wherein the accelerator applications prepare the predicted documents or information for delivery to the authenticated entity prior to the receipt of a request for the predicted electronic documents or information from the authenticated entity;
(u) wherein the information sent and received via the method by authenticated entities is restricted to health information and other information used in delivering healthcare services or related thereto; and
(v) wherein the entities authenticated for participating in the method are healthcare providers, healthcare provider organizations, patients and the authorized representatives of these entities.

\* \* \* \* \*